(12) United States Patent
Collazo

(10) Patent No.: US 9,033,902 B2
(45) Date of Patent: May 19, 2015

(54) FEMORAL CONDYLAR RADIUS GAGE

(75) Inventor: Carlos E. Collazo, Old Greenwich, CT (US)

(73) Assignee: Howmedica Osteonics Corp., Mahwah, NJ (US)

(*) Notice: Subject to any disclaimer, the term of this patent is extended or adjusted under 35 U.S.C. 154(b) by 318 days.

(21) Appl. No.: 13/597,409

(22) Filed: Aug. 29, 2012

(65) Prior Publication Data

US 2014/0066809 A1   Mar. 6, 2014

(51) Int. Cl.
| A61B 5/103 | (2006.01) |
| A61B 5/107 | (2006.01) |
| A61B 5/00 | (2006.01) |
| A61F 2/46 | (2006.01) |

(52) U.S. Cl.
CPC .......... *A61B 5/1072* (2013.01); *A61B 5/4887* (2013.01); *A61F 2/4657* (2013.01); *A61B 2505/05* (2013.01); *A61B 5/4585* (2013.01)

(58) Field of Classification Search
None
See application file for complete search history.

(56) References Cited

U.S. PATENT DOCUMENTS

| 181,809 | A | 9/1876 | Williams |
| 1,878,439 | A | 2/1908 | Wagniere |
| 2,362,907 | A | 11/1944 | Levin |
| 3,391,465 | A | 7/1968 | Eidam |
| 3,754,335 | A | 8/1973 | Culbertson |
| 4,596,076 | A | 6/1986 | Sigg |
| 5,077,908 | A | 1/1992 | Moore |
| 5,925,049 | A | * | 7/1999 | Gustilo et al. ............ 606/82 |
| 6,096,043 | A | 8/2000 | Techiera et al. |
| 6,106,529 | A | 8/2000 | Techiera |
| 6,159,217 | A | 12/2000 | Robie et al. |
| 7,497,027 | B2 | 3/2009 | Waltz, Jr. |
| 7,527,631 | B2 | 5/2009 | Maroney et al. |
| 7,572,262 | B1 | 8/2009 | Hoeppner et al. |
| 2010/0186250 | A1* | 7/2010 | Hu .............................. 33/807 |

FOREIGN PATENT DOCUMENTS

WO    WO 2011141723 A1  *  11/2011

* cited by examiner

*Primary Examiner* — Brian Szmal
*Assistant Examiner* — Matthew Kremer
(74) *Attorney, Agent, or Firm* — Lerner, David, Littenberg, Krumholz & Mentlik, LLP

(57) ABSTRACT

An instrument and method for determining the location of the anatomical epicondylar axis between the condyles of a femur is provided. The instrument includes first and second gauges each for measuring a radius of a femoral condyle and a frame. At least one of the gauges is movably connected to the frame. The method includes positioning the measuring end of each gauge against a separate condyle of a femur, actuating a pivoting member of each gauge to determine the radius of each condyle, measuring the distance between the condyles, and determining the location of the anatomical epicondylar axis of the femur. A measurement can be taken from a measuring scale provided on the gauge and from another scale provided on the frame. Determining the location of the axis can further include performing a calculation utilizing the radii of the condyles and the distance between the condyles.

20 Claims, 6 Drawing Sheets

FEMORAL CONDYLAR RADIUS GAGE

BACKGROUND OF THE INVENTION

Total knee replacement ("TKR") requires many surgical steps and intraoperative decisions for a successful outcome. One of the steps requires the prosthesis to be rotationally aligned with the epicondylar or flexion axis of the distal end of the femur. The epicondylar axis is generally believed to be externally rotated approximately three degrees with respect to the posterior condyles. However, this is only an approximation since the actual value varies from patient to patient. Additionally, it is very difficult to definitively identify the epicondylar axis because its origin, the insertion sites of the medial and lateral collateral ligaments, is not an exact point, but rather an area of attachment. Therefore, current TKR procedures approximate the epicondylar axis in a visual manner as opposed to actually measuring the position of the axis.

Except for computer-assisted navigated TKR, there currently exists no instrumented means of measuring the curvature of the condyles of a knee. The present invention relates to an apparatus used to measure the radius value of a curved surface of a knee as well as an improved method of determining the flexion axis of a knee.

Current non-computer assisted method of rotational alignment rely on the epicondylar axis or referencing of the posterior condyles. These instruments are either set at a fixed angle or adjustable. Whether fixed or adjustable, the surgeon has no idea what that specific patient's natural anatomic angle of external rotation is and will ultimately result in suboptimal placement of the component.

BRIEF SUMMARY OF THE INVENTION

A first aspect of the present invention is an instrument for determining the location of the anatomical epicondylar axis between the condyles of a femur. The instrument includes a frame and first and second gauges each for measuring a radius of a femoral condyle, each gauge including a measuring end and a display end, each gauge further including a body having adjacent the measuring end a first surface and a second surface angled with respect to the first surface. At least one of the first and second gauges is movably connected to the frame.

In accordance with certain embodiments of this first aspect, each gauge may be configured to respectively contact a first and second femoral condyle. Each gauge may be connected to the frame at the display end. The frame may further include a measuring scale for determining a distance between portions of the frame at which the first and second gauges are connected.

Each gauge may further include a pivoting member pivotally connected to the body, the pivoting member having a bone-contacting end at the measuring end of the gauge and an indicator end at the display end of the gauge. The pivoting member of each gauge may be pivotally connected to the respective body at a pivot point between the measuring end and the display end of the gauge, such that the indicator end of the pivoting member is in communication with a measuring scale provided on the display end of the body to provide a measurement. The measurement may be determined by a location of the bone-contacting end of the pivoting member with respect to the first and second surfaces of the body. The body of each gauge may include an aperture at a junction between the first and second surfaces, and the bone-contacting end of the pivoting member is configured to extend through the aperture. At least one of the first and second gauges may further include a spring disposed between the body and the pivoting member, such that the bone-contacting end of the pivoting member is biased into the aperture.

A second aspect of the present invention is an instrument for determining the location of the anatomical epicondylar axis between the condyles of a femur. The instrument includes a frame and first and second gauges for measuring a radius of a femoral condyle, each gauge including a measuring end, a display end, a body, and a pivoting member pivotally connected to the body, the body having adjacent the measuring end a first surface and a second surface angled with respect to the first surface, the pivoting member having a bone-contacting end at the measuring end of the gauge and an indicator end at the display end of the gauge. The body of at least one of the first and second gauges is movably connected to the frame. The pivoting member of each gauge is pivotally connected to the respective body at a pivot point between the measuring end and the display end of the gauge, such that the indicator end of the pivoting member is in communication with a measuring scale provided on the display end of the body to provide a measurement. The body of each gauge includes an aperture at a junction between the first and second surfaces, and the bone-contacting end of the pivoting member is configured to extend through the aperture.

A third aspect of the present invention is a method for determining the location of the anatomical epicondylar axis between the condyles of a femur. The method includes the steps of providing an instrument including first and second gauges each for measuring a radius of a femoral condyle, each gauge including a measuring end and a display end, each gauge further including a body and a pivoting member pivotally connected to the body, the pivoting member having a bone-contacting end at the measuring end of the gauge; positioning the measuring end of each gauge against a separate condyle of a femur; actuating the pivoting member of each gauge with respect to the body so that the bone-contacting end of the pivoting member contacts the posterior surface of the condyle; determining the radius of each condyle; measuring the distance between the condyles; and determining the location of the anatomical epicondylar axis of the femur.

In accordance with certain embodiments of this third aspect, the instrument may further include a frame and at least one of the first and second gauges being movably connected to the frame, and the step of measuring may include taking a measurement from a measuring scale of the frame to determine a distance between portions of the frame at which the first and second gauges are connected, respectively. The step of positioning may further include adjusting the position of at least one of the first and second gauges with respect to the frame. The step of positioning may include placing first and second surfaces of each body which are angled with respect to one another against the curved surface of the condyle. The pivoting member may further include an indicator end at the display end of the gauge, and the step of determining the radius may include taking a measurement from a measuring scale provided on the body at the display end of the gauge, the measurement corresponding to the position of the indicator end with respect to the measuring scale.

The step of determining the radius may include extending the bone-contacting end of the pivoting member through an aperture at a junction between the first and second surfaces and contacting the condyle with the bone-contacting end. The step of determining the radius may further include measuring the distance between a contact point between the bone-contacting end of the pivoting member and an apex of an angle formed between the first and second surfaces of the body. At least one of the first and second gauges may include a spring disposed between the body and the pivoting member such that the bone-contacting end of the pivoting member is biased into the aperture, and the step of determining the radius may further include allowing the spring to force the bone-contacting end into contact with the femoral condyle.

The step of determining the location may include performing a calculation utilizing the radii of the condyles and the distance between the condyles. The step of determining the location may further include performing a calculation utilizing a first measurement from a measuring scale of the frame to determine a distance between portions of the frame at which the first and second gauges are connected, respectively, and second and third measurements from measuring scales provided on the bodies at the display ends thereof corresponding to the position of the indicator end with respect to the body. The step of determining the location may include obtaining the numerical values of the radii of the femoral condyles and the distance between the condyles and determining the location of the epicondylar axis by referencing a chart.

DETAILED DESCRIPTION

Existing non-computer navigated methods of identifying the flexion axis of the femur are highly inaccurate and unrepeatable. The present instrumented method can precisely measure the center of the flexion-extension radius of the distal femur and can subsequently enable a femoral component of a prosthesis to be accurately aligned to the patient's anatomy.

Figure 5:
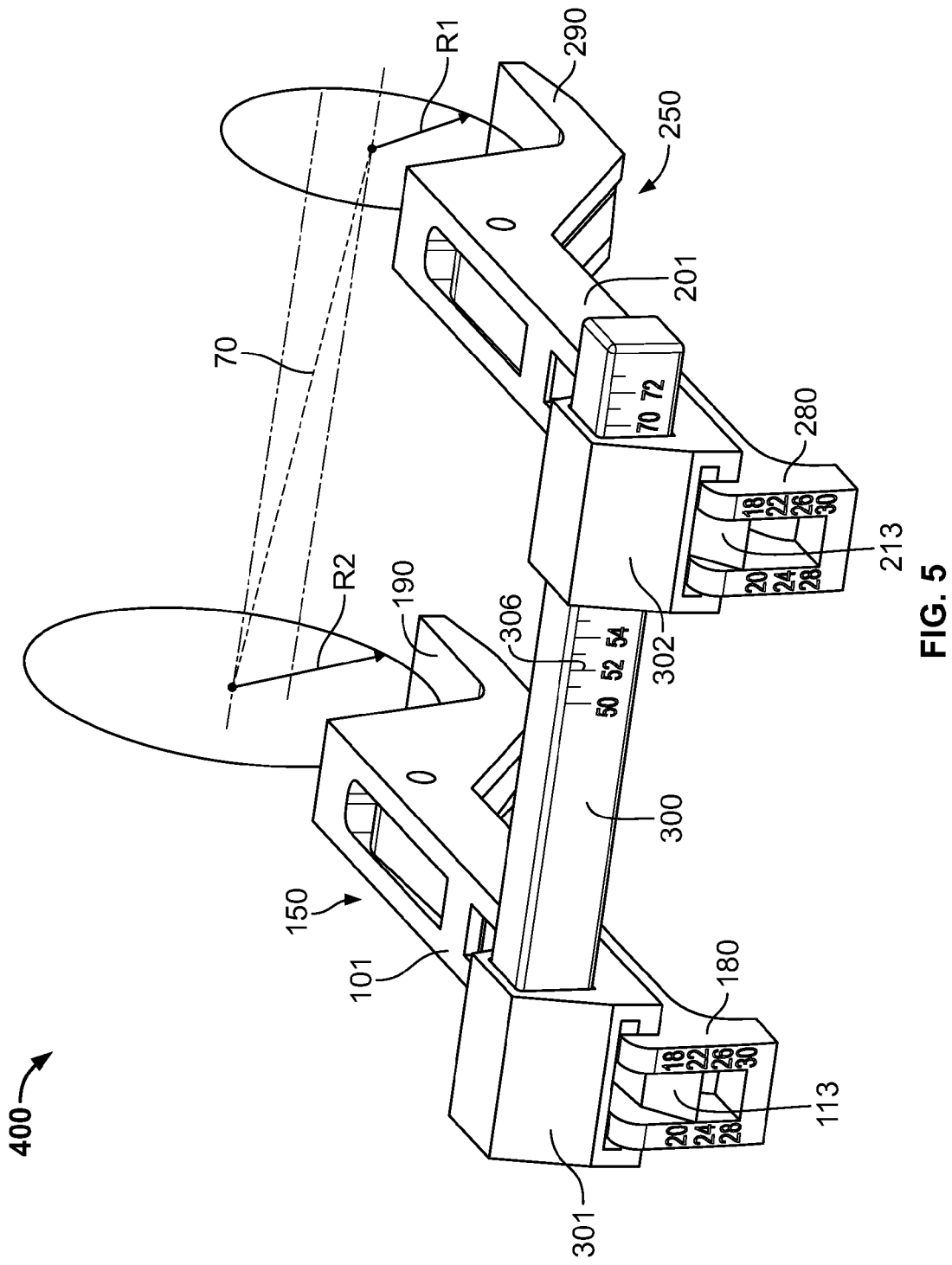
FIG. 5 is a perspective view of the instrument including the gauge shown in FIG. 1, a second gauge, and a frame.

An instrument 400 in accordance with an embodiment of the present invention is shown in FIG. 5. Instrument 400 includes a first gauge 150, a second gauge 250, and a frame 300. The components of instrument 400 will be described in turn below.

Shown in FIGS. 1-4 is a gauge 50, similar in nature to gauges 150 and 250, that is used for measuring a radius of a femoral condyle. Gauge 50 includes a main housing 1, a pivoting member 2, a pivot pin 3, and a compression spring 4, and defines a display end 80 and a measuring end 90. Housing 1 is a longitudinal body extending between measuring end 90 and display end 80. Housing 1 is generally configured with a channel 6 in which pivoting member 2 can be positioned. Channel 6 is generally disposed along the body and extending between ends 80 and 90. Two opposing sides 7 and 8 provide structure for housing 1 and are disposed on either side of channel 6. A bore or hole is provided in each of sides 7 and 8 into which pivot pin 3 can be inserted. Extending between sides 7 and 8 is a bar 22 that interfaces with spring 4 at its end surface 5, which may be flat or may include a recess or counterbore to cooperate more securely with spring 4.

Figure 1:
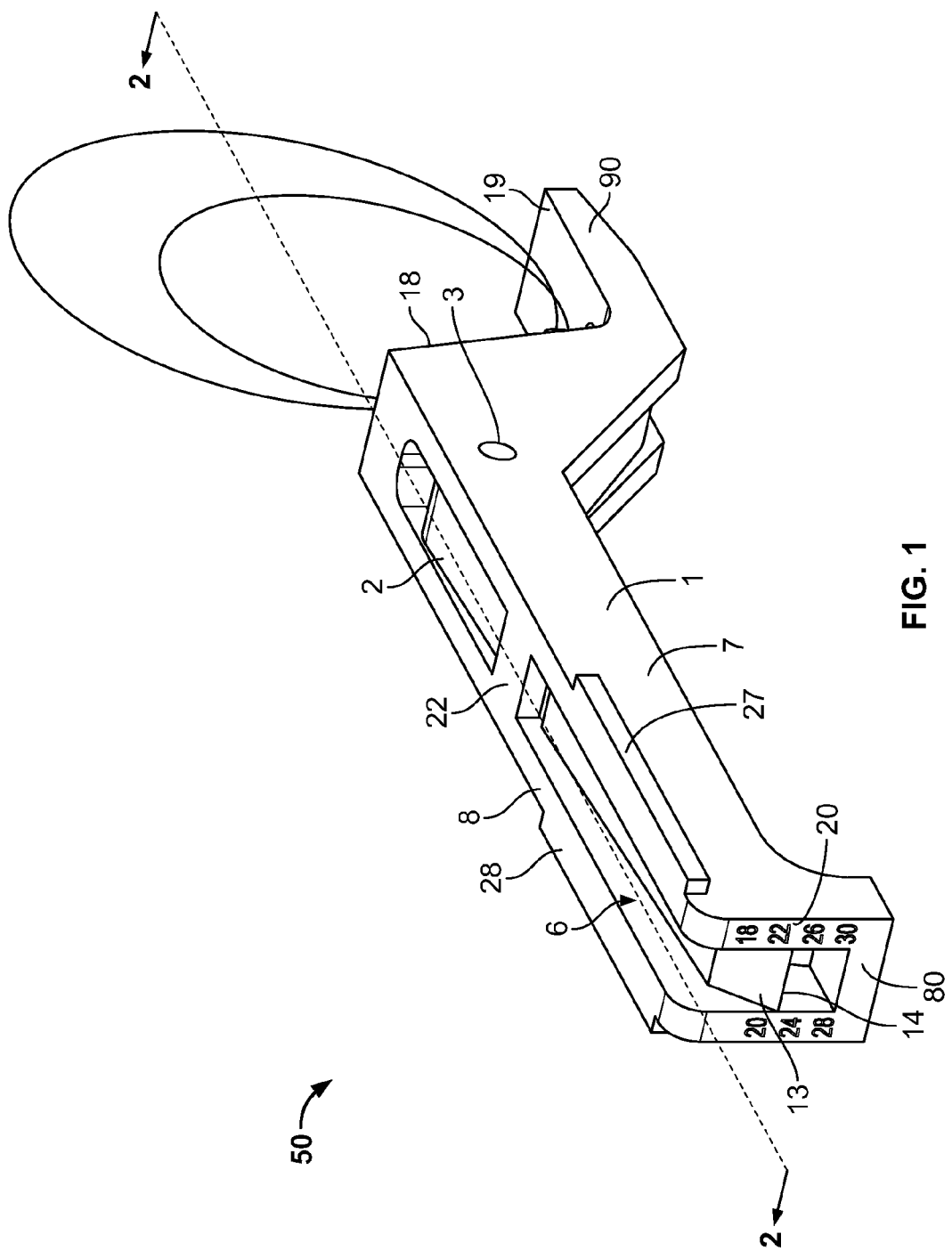
FIG. 1 is a perspective view of a gauge of an instrument for determining the location of the anatomical epicondylar axis between the condyles of a femur accordance with an embodiment of the present invention.
Figure 2:
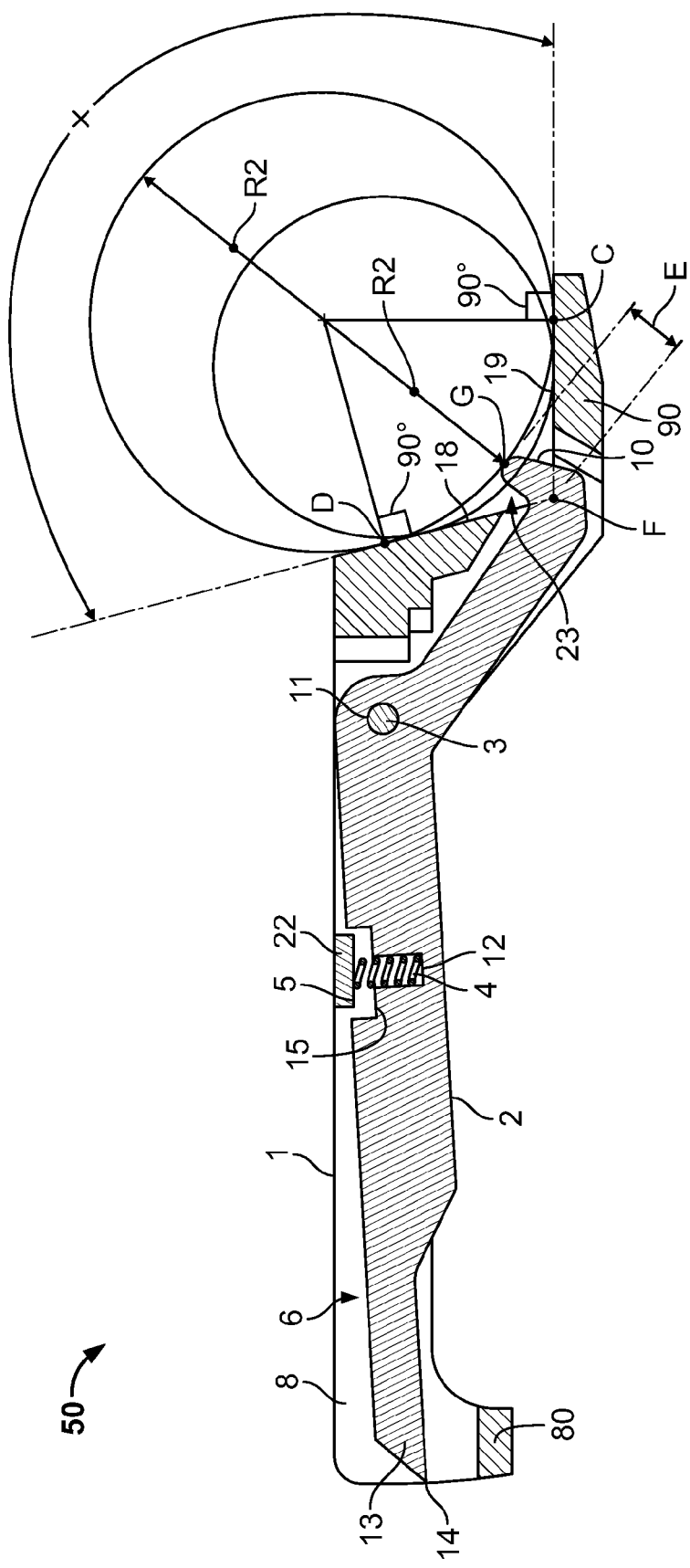
FIG. 2 is a side sectional view of the gauge shown in FIG. 1 taken along the line 2-2.
Figure 4:
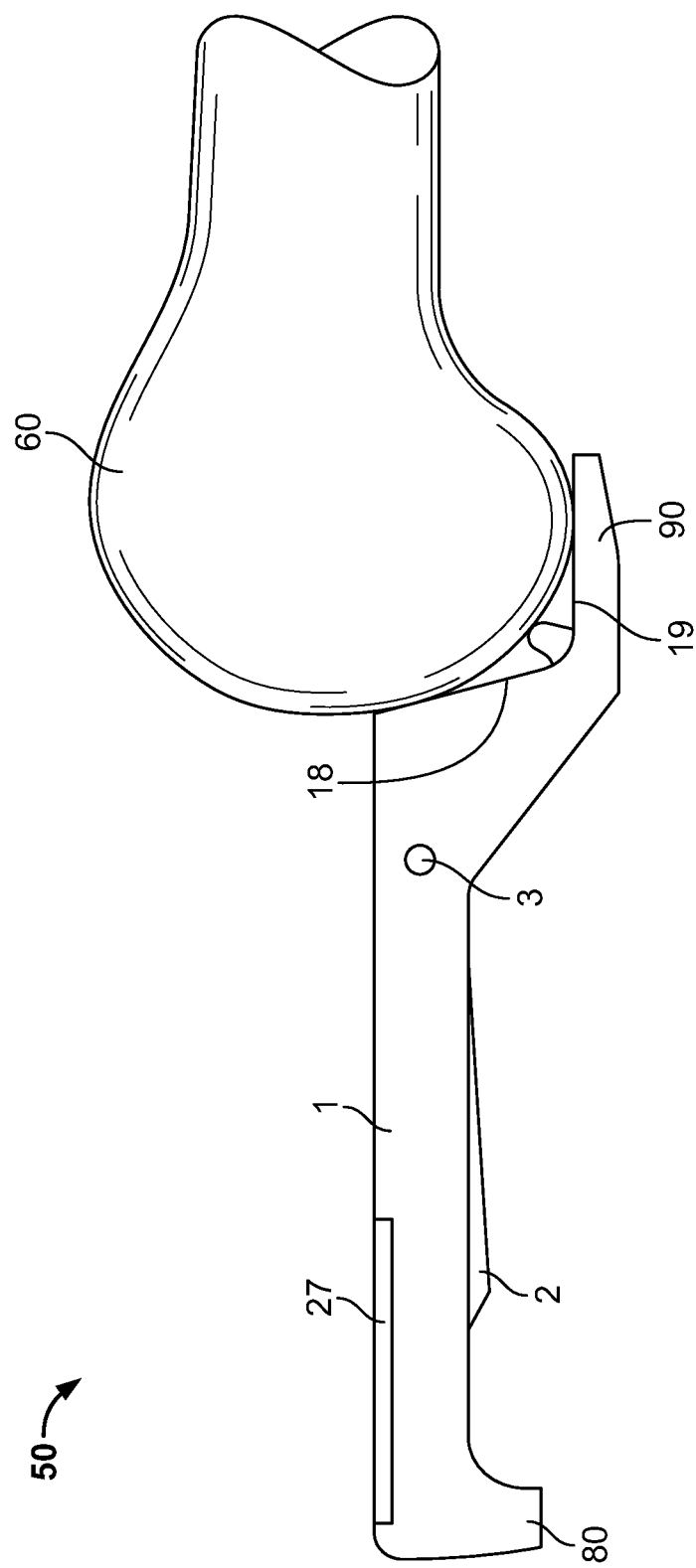
FIG. 4 is a side elevational view of the gauge shown in FIG. 1 in use next to the distal end of a femur.

Measuring end 90 of housing 1 includes a first surface 18 and a second surface 19 that are fixed and angled with respect to one another to form therebetween an angle X, as shown in FIG. 2. Surfaces 18 and 19 are configured for contacting portions of a round surface, such as the distal end of a femur 60, as shown in FIG. 4. Surfaces 18 and 19 are preferably oriented such that angle X is between about ninety (90°) and one hundred thirty-five degrees (135°), although angle X could be any angle between zero (0°) and one hundred eighty degrees (180°) that allows gauge 50 to be constructed and utilized according to the present invention. At measuring end 90, channel 6 intersects surfaces 18 and 19 at an aperture 23, which is disposed at a junction between surfaces 18 and 19. Proximal to display end 80, wings 27 and 28 are formed on either side of housing 1 extending from sides 7 and 8, respectively, and are used to connect external components to gauge 50, as discussed below. Display end 80 of housing 1 is open to channel 6, and can contain a scale, such as markings shown in FIG. 1, on either or both of sides 7 and 8. Markings 20 can allow the user to read a measurement taken by gauge 50.

Pivoting member 2 is a longitudinal body having a bone-contacting end 10 adjacent measuring end 90 and an indicator end 13 adjacent display end 80. Pivoting member 2 includes a bore or hole 11 at a location between ends 10 and 13 that accepts pivot pin 3. When assembled with housing 1 via pivot pin 3, pivoting member 2 can be pivoted with respect to housing 1 about the axis through pivot pin 3. Thus, pivot pin 3 marks the fixed center of rotation between member 2 and housing 1. At a middle portion of pivoting member 2 between ends 10 and 13, a recess 15 and a counterbore 12 are provided. Recess 15 cooperates with bar 22 so that the upper surfaces of bar 22, sides 7 and 8, and pivoting member 2 can be substantially flush or planar in a certain configuration. Counterbore 12 is configured to cooperate and interface with spring 4.

Figure 3:
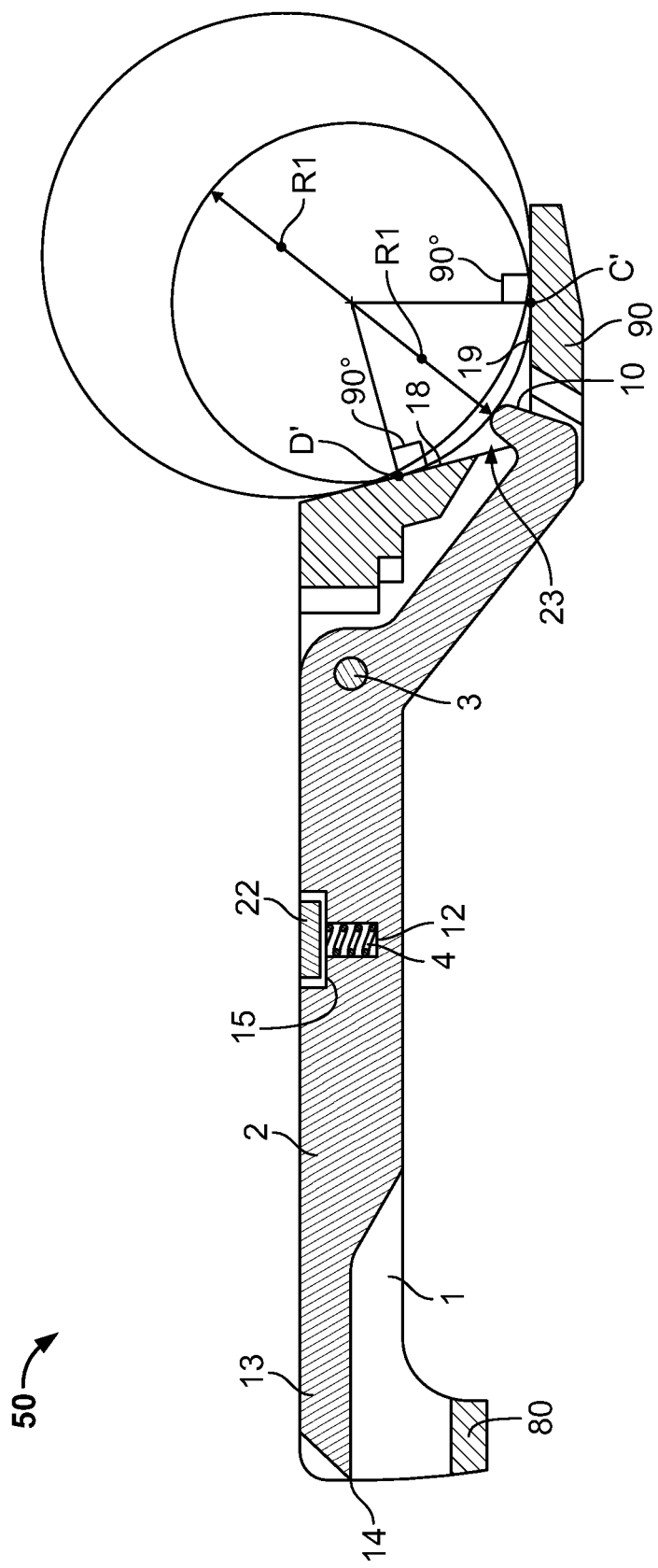
FIG. 3 is another side sectional view of the gauge shown in FIG. 1 with the pivoting member in another position with respect to the housing.

When gauge 50 is assembled such that housing 1 and pivoting member 2 are connected via pivot pin 3, spring 4 is disposed within counterbore 12 and is positioned between end surface 5 of bar 22 and the bottom surface of counterbore 12, as shown in FIGS. 2 and 3. Spring 4 is biased to force bar 22 from counterbore 12, which, when spring 4 expands, causes pivoting member 2 to rotate with respect to housing 1 about pin 3. This rotation biases pivoting member from an initial position shown in FIG. 3 to a secondary position shown in FIG. 2. Spring 4 therefore biases bone-contacting end 10 to extend through aperture 23. Indicator end 13 of pivoting member 2 is positioned adjacent to display end 80 of housing 1 such that an edge 14 of indicator end 13 is in communication with markings 20. Edge 14 can thusly translate a particular position of pivoting member 2 with respect to housing 1 by indicating a marking 20 to provide a measurement. In other words, a position of bone-contacting end 10 with respect to housing 1 corresponds to a particular position of indicator end 13 with respect to housing 1, which can be indicated at the measuring scale, or markings 20. Markings 20 are precisely located on display end 80 of housing 1 based on a known unit of measurement and based on the relationship between the position of bone-contacting end 10 with respect to surfaces 18 and 19. Markings 20 are preferably measured in millimeters, but can be measured in any suitable unit of measurement.

Housing 1 and pivoting member 2 are each preferably comprised of a material that is rigid and monolithic, or comprised of one-piece, though each can be made of multiple parts. It will be appreciated that the rigid nature of each component allows the relationship between such components at measuring end 90 to be substantially exactly translated into a measurement indication at display end 80.

A method of using gauge 50 includes placing surfaces 18 and 19 of gauge 50 against a curved surface, such as the posterior condyle of a femur 60, as shown in FIG. 4. The curved surface of the bone upon contact with measuring end 90 of gauge 50 will be tangent in two locations, depicted as points C and D in FIG. 2. Pivoting member 2 is rotated about pin 3 until bone-contacting end 10 extends through aperture 23 and comes into contact with the adjacent portion of bone. Since angle X of gauge 50 shown in FIG. 2 is constant, the locations of points C and D will vary depending on whether the bone radius is larger or smaller. The bone radius R2 depicted in FIG. 2 is relatively larger than the bone radius R1 depicted in FIG. 3, which contacts surfaces 19 and 18 at points C' and D', respectively.

While the bone is positioned against surfaces 18 and 19, gauge 50 measures the particular radius of the bone by contacting a third portion of the bone with bone-contacting end 10 of pivoting member 2. For differently-sized bones, the points of contact between the bone and surfaces 18 and 19 (C and D, C' and D', etc.) will correspond with a particular location G at which bone-contacting end 10 contacts the bone. As shown in FIG. 2, distance E is measured from an apex F, which is the location at which surfaces 18 and 19 coincide, to point G, which is the location on the bone that lies on the circumference of the circle passing through points C and D, shown in FIG. 2. While apex F technically extends along an axis because of the planar nature of surfaces 18 and 19, apex F can be considered a point insofar as pivoting member passes through the point of apex F and contacts a portion of the bone at point G, both of which are in the plane of the sectional view shown in FIG. 2. While the location of apex F is known to gauge 50, the distance bone-contacting end 10 must travel before contacting the posterior surface of the bone at point G is measured by gauge 50 to determine the measurement of E. Pivoting member is calibrated such that upon contact between bone-contacting end 10 and the posterior surface of the bone, edge 14 of indicator end 13 of pivoting member is aligned with respect to markings 20 such that markings 20 can indicate the measurement of the radius of the bone, and the user can simply read such measurement from display end 80. Thus, as shown in FIG. 1, edge 14 points to a marking of markings 20, which in turn provides the value of the radius, for example, in millimeters.

The influence of spring 4 between housing 1 and pivoting member 2 is such that pivoting member 2 is biased to extend to the maximum value of distance E achievable by gauge 50. Therefore, once a bone is placed in contact with surfaces 18 and 19, the bone will tend to force bone-contacting end 10 back toward aperture 23. Bone-contacting end 10 will therefore maintain contact with the bone under the influence of spring 4. Because a femoral condyle is not perfectly cylindrical or perfectly spherical, gauge 50 can be moved into various positions about the general circumference of the femoral condyle. The slight variation of pivoting member 2 during the movement can allow the user to determine the most appropriate value of the general radius of the bone. In other words, the different values of the radius that are measured at different locations of the bone can be recorded and synchronized to determine a general value of the radius of the bone. Again, spring 4 is loaded to ensure sufficient contact between pivoting member 2 and bone during measurement.

Of course, it will be understood that the construction of gauge 50 is such that bone-contacting end 10 of pivoting member 2 does not travel along a straight line between apex F and its point of contact with the bone. Rather, bone-contacting end 10 travels along a slightly arcuate path due to the rotation of pivoting member 2 about pivot pin 3. The influence of the arc of the path is slight, and can be taken into account so that markings 20 are prepared to provide an accurate indication of the radius despite the non-linear path of bone-contacting end 10. Such considerations can be made during manufacture of gauge 50 based on the dimensions of its components.

As the distance between pin 3 and end 13 is longer than the distance between pin 3 and bone-contacting end 10, the movement of indicator end 13 is greater than the movement at bone-contacting end 10, which results in greater precision and resolution for easier reading of gauge 50 by the user. Thus, as the difference between the measurements of two condyles can be quite small, indicator end 13 allows for more pronounced distinction between different measurements.

The correlation between the geometric calculations with respect to distance E, angle X, and a radius of bone, such as radius R1 or R2, and the associated markings 20 is done through CAD logistics and analysis. The resulting values of the measurements are incorporated into the blueprints for manufacturing gauge 50. The user of the device will simply measure the bone and get a radius value for that bone.

As shown in FIG. 5 and according to the present invention, instrument 400 includes first and second gauges 150 and 250, each of which is similar in nature to the above-described gauge 50. Gauges 150 and 250 are connected to frame 300 to form instrument 400. Housing 101 and housing 201 are each connected to frame 300 adjacent the respective display end 180 and 280. Frame 300 allows calibrated translation of gauges 150 and 250 along the medial-lateral direction. In certain embodiments, such as that shown in FIG. 5, a first connector 301 and a second connector 302 may be used to attach frame 300 to housings 101, 201, respectively. Frame 300 can be slid into each connector 301 and 302 along the axis of frame 300 and anchored thereto in a fixed or sliding relationship. Alternatively, one of connectors 301 and 302 can be manufactured in connection with frame 300 so that the connector and frame 300 form a single monolithic, or one-piece, component. Preferably, at least one of connectors 301 and 302 is movable with respect to frame 300 while the other connector is fixedly attached thereto. Thus, one connector can be moved with respect to the other along frame 300 and the distance between the connectors can be measured. In other embodiments, both connectors 301 and 302 can be movable with respect to frame 300.

Instrument 400 can be used to determine the location of the anatomical epicondylar axis between the condyles of a femur. In use, instrument 400 is assembled such that each gauge 150, 250 is configured to respectively contact a first and second femoral condyle. This is done by attaching each gauge 150, 250 to a connector 301 and 302 such that the distance between gauges 150 and 250 is variable. The housing 101, 201 of each gauge 150, 250 can connect to a connector 301, 302 via engagement between wings (27, 28 in gauge 50 above) and a corresponding portion of the respective connector 301, 302. This engagement can be made by sliding the connector onto the gauge. In alternate embodiments, either or both of connectors 301, 302 may be manufactured in connection with gauges 150, 250, respectively, to form monolithic structures. In other embodiments, gauges 150, 250 may be configured to attach with frame 300 without the use of connectors 301, 302.

During use of instrument 400, the position of either or both gauges 150, 250 can be adjusted along frame 300 accordingly to ensure a proper connection with the respective condyle. Frame 300 can include a measuring scale 306 for determining a distance between portions of frame 300 at which first and second gauges 150, 250 are connected. This measurement is preferably the distance between the central portions of gauges 150, 250, and is most accurate when referencing a housing or connector that is fixedly anchored to frame 300 while the other can slide along scale 306 to indicate a measurement. In other embodiments of instrument 400 where both gauges 150, 250 are moveably connected to frame 300, alternative measuring systems can be used, such as simply measuring the distance between the gauges on an unmarked frame, for example by using an external measuring device. The measuring end 190, 290 of each gauge 150, 250, respectively, is positioned against a separate condyle of a femur as shown in FIG. 5, and the gauges 150 and 250 are each operated in a manner as described above to determine the radius of each femoral condyle. The distance between the condyles is then measured by determining the distance between the first and second gauges 150, 250, and in particular, by reading such measurement from scale 306 on frame 300.

Figure 6:
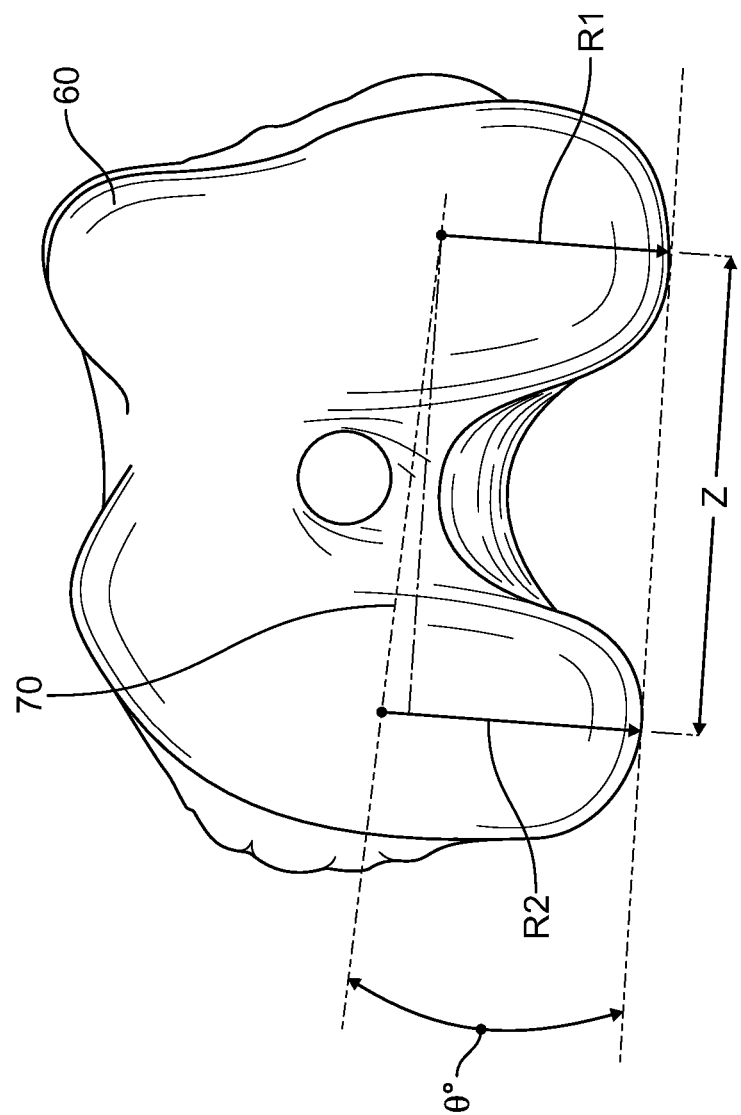
FIG. 6 is an elevational view of the distal end of a femur.

Finally, the location of the anatomical epicondylar axis of the femur can be determined through a calculation using the measured values shown in connection with femur 60 in FIG. 6, including the radii R1 and R2 of the condyles and the distance Z between the condyles. Of course, the distance Z corresponds to a first measurement from measuring scale 306 of frame 300 to determine a distance between portions of the frame at which the first and second gauges are connected, respectively. Similarly, the second and third measurements of R1 and R2 are from measuring scales 120, 220 provided on housings 101, 201 at display ends 180, 280 thereof corresponding to the position of indicator ends 113, 213 with respect to housings 101, 201. Once the values of R1, R2, and Z are obtained, determining the location of the epicondylar axis 70 can be done by referencing a chart giving the rotation of the epicondylar axis.

Alternatively, the natural anatomic rotation of the epicondylar axis 70 can be calculated trigonometrically using the values of the radii of the condyles and the distance between the condyles. The radius of the posterior medial condyle is generally larger than that of the posterior lateral condyle. Using the following trigonometric formula, the rotation is determined. The angle is equal to the arctangent of a quantity, that quantity being the difference between the radii (R2 minus R1) divided by the distance between the condyles (Z). The difference between the radii should be computed subtracting the radius of the lateral condyle from that of the medial condyle. In any event, the absolute value of the difference should be used.

In another embodiment according to the present invention, a single gauge can be used exclusive of the other components. Using a first method, the measurement site on each condyle can be marked using a bovie or a methylene blue marker and the medial-lateral distance between the marks can be measured. The rotation of the epicondylar axis 70 can then be calculated as described above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An instrument for determining a location of an anatomical epicondylar axis between condyles of a femur, the instrument comprising:

first and second gauges each for measuring a radius of a femoral condyle, each gauge including a measuring end, a display end, a body, and a pivoting member pivotally connected to the body, the body having adjacent the measuring end a first surface and a second surface angled with respect to the first surface, the pivoting member having a bone-contacting end at the measuring end of the gauge and an indicator end at the display end of the gauge; and a frame, wherein at least one of the first and second gauges is movably connected to the frame.

2. The instrument of claim 1, wherein each gauge is configured to respectively contact a first and second femoral condyle.

3. The instrument of claim 1, wherein each gauge is connected to the frame at the display end.

4. The instrument of claim 1, wherein the frame further comprises a measuring scale for determining a distance between portions of the frame at which the first and second gauges are connected.

5. The instrument of claim 1, wherein the pivoting member of each gauge is pivotally connected to the respective body at a pivot point between the measuring end and the display end of the gauge, such that the indicator end of the pivoting member is in communication with a measuring scale provided on the body adjacent the display end of the gauge to provide a measurement.

6. The instrument of claim 5, wherein the measurement is determined by a location of the bone-contacting end of the pivoting member with respect to the first and second surfaces of the body.

7. The instrument of claim 1, wherein the body of each gauge includes an aperture at a junction between the first and second surfaces, and the bone-contacting end of the pivoting member is configured to extend through the aperture.

8. The instrument of claim 7, wherein at least one of the first and second gauges further includes a spring disposed between the body and the pivoting member, such that the bone-contacting end of the pivoting member is biased into the aperture.

9. An instrument for determining a location of an anatomical epicondylar axis between condyles of a femur, the instrument comprising:

first and second gauges each for measuring a radius of a femoral condyle, each gauge including a measuring end, a display end, a body, and a pivoting member pivotally connected to the body, the body having adjacent the measuring end a first surface and a second surface angled with respect to the first surface, the pivoting member having a bone-contacting end at the measuring end of the gauge and an indicator end at the display end of the gauge; and a frame, wherein the body of at least one of the first and second gauges is movably connected to the frame, wherein the pivoting member of each gauge is pivotally connected to the respective body at a pivot point between the measuring end and the display end of the gauge, such that the indicator end of the pivoting member is in communication with a measuring scale provided on the body adjacent the display end of the gauge to provide a measurement, and wherein the body of each gauge includes an aperture at a junction between the first and second surfaces, and the bone-contacting end of the pivoting member is configured to extend through the aperture.

10. A method for determining a location of an anatomical epicondylar axis between condyles of a femur, the method comprising the steps of:

providing an instrument including first and second gauges each for measuring a radius of a femoral condyle, each gauge including a measuring end and a display end, each gauge further including a body and a pivoting member pivotally connected to the body, the pivoting member having a bone-contacting end at the measuring end of the gauge;

positioning the measuring end of each gauge against a separate condyle of a femur;

actuating the pivoting member of each gauge with respect to the body so that the bone-contacting end of the pivoting member contacts a surface of the condyle;

determining a radius of each condyle using the instrument;

measuring a distance between the condyles using the instrument; and determining the location of the anatomical epicondylar axis of the femur utilizing the radii of the condyles and the distance between the condyles.

11. The method of claim 10, wherein the instrument further includes a frame and at least one of the first and second gauges being movably connected to the frame, and wherein the step of measuring includes taking a measurement from a measuring scale of the frame to determine a distance between portions of the frame at which the first and second gauges are connected, respectively.

12. The method of claim 11, wherein the step of positioning further includes adjusting a position of at least one of the first and second gauges with respect to the frame.

13. The method of claim 10, wherein the step of positioning includes placing first and second surfaces of each body which are angled with respect to one another against a curved surface of the condyle.

14. The method of claim 10, wherein the pivoting member further includes an indicator end at the display end of the gauge, and the step of determining the radius includes taking a measurement from a measuring scale provided on the body at the display end of the gauge, the measurement corresponding to a position of the indicator end with respect to the measuring scale.

15. The method of claim 10, wherein the step of determining the radius includes extending the bone-contacting end of the pivoting member through an aperture at a junction between first and second surfaces of each body which are angled with respect to one another against a curved surface of the condyle and contacting the condyle with the bone-contacting end.

16. The method of claim 15, wherein the step of determining the radius further includes measuring a distance between a contact point between the bone-contacting end of the pivoting member and an apex of an angle formed between the first and second surfaces of the body.

17. The method of claim 15, wherein at least one of the first and second gauges includes a spring disposed between the body and the pivoting member such that the bone-contacting end of the pivoting member is biased into the aperture, and wherein the step of determining the radius further includes allowing the spring to force the bone-contacting end into contact with the femoral condyle.

18. The method of claim 10, wherein the step of determining the location includes performing a calculation utilizing the radii of the condyles and the distance between the condyles.

19. The method of claim 10, wherein the step of determining the location further includes performing a calculation utilizing a first measurement from a measuring scale of the frame to determine a distance between portions of the frame at which the first and second gauges are connected, respectively, and second and third measurements from measuring scales provided on the bodies at the display ends thereof corresponding to positions of indicator ends of the respective pivoting members with respect to the body.

20. The method of claim 10, wherein the step of determining the location includes obtaining numerical values of the radii of the femoral condyles and the distance between the condyles and determining the location of the epicondylar axis by referencing a chart.

\* \* \* \* \*